US008652101B2

(12) United States Patent
Müller et al.

(10) Patent No.: US 8,652,101 B2
(45) Date of Patent: Feb. 18, 2014

(54) IMPLANTATION DEVICE FOR METABOLITE SENSORS

(75) Inventors: Achim Müller, Grossostheim (DE); Peter Herbrechtsmeier, Königstein (DE)

(73) Assignee: EyeSense AG, Basel (CH)

( * ) Notice: Subject to any disclaimer, the term of this patent is extended or adjusted under 35 U.S.C. 154(b) by 190 days.

(21) Appl. No.: 13/122,110

(22) PCT Filed: Oct. 2, 2009

(86) PCT No.: PCT/EP2009/062824
§ 371 (c)(1),
(2), (4) Date: May 31, 2011

(87) PCT Pub. No.: WO2010/037848
PCT Pub. Date: Apr. 8, 2010

(65) Prior Publication Data
US 2011/0230835 A1    Sep. 22, 2011

(30) Foreign Application Priority Data
Oct. 2, 2008  (EP) .................................... 08165704

(51) Int. Cl.
*A61M 37/00*   (2006.01)
(52) U.S. Cl.
USPC ......................................................... 604/150
(58) Field of Classification Search
USPC ......................................................... 604/150
See application file for complete search history.

(56) References Cited

U.S. PATENT DOCUMENTS

| 5,370,611 | A  | * | 12/1994 | Niezink et al. ................... 604/62 |
| 6,261,245 | B1 |   | 7/2001  | Kawai et al. |
| 6,496,561 | B1 | * | 12/2002 | Meyer et al. ..................... 378/65 |
| 7,226,414 | B2 |   | 6/2007  | Ballerstadt et al. |
| 2007/0122829 | A1 |   | 5/2007  | Ballerstadt et al. |
| 2007/0173706 | A1 | * | 7/2007  | Neinast et al. ................ 600/309 |
| 2008/0139903 | A1 |   | 6/2008  | Bruce et al. |
| 2011/0137255 | A1 |   | 6/2011  | Nielsen et al. |

FOREIGN PATENT DOCUMENTS

| CN | 1223847 | 7/1999 |
| CN | 1874809 | 12/2006 |
| WO | WO-94/04217 | 3/1994 |
| WO | WO-99/44687 | 9/1999 |

(Continued)

OTHER PUBLICATIONS

PCT International Search Report in PCT/EP2009/062824, dated Jan. 27, 2010, 3 pgs.

(Continued)

*Primary Examiner* — Jason Flick
(74) *Attorney, Agent, or Firm* — Servilla Whitney LLC

(57) ABSTRACT

The invention relates to an implantation device for implanting a sensor element for detecting at least one analyte in a bodily fluid or body tissue. The implantation device comprises at least one cannula for piercing a skin surface of a patient. The cannula has at least one holding area for holding the sensor element. The implantation device furthermore has at least one hydraulic container, connected to the cannula, for holding a hydraulic fluid and at least one pressure generation device. The pressure generation device is designed to apply pressure to the hydraulic fluid, wherein the sensor element can be transferred from the cannula into the body tissue using the hydraulic fluid.

28 Claims, 2 Drawing Sheets

(56) References Cited

FOREIGN PATENT DOCUMENTS

| WO | WO-01/13783 | 3/2001 |
| WO | WO-02/087429 | 11/2002 |
| WO | WO-2005/054831 | 6/2005 |
| WO | WO-2007/058921 | 5/2007 |

OTHER PUBLICATIONS

PCT IPRP in PCT/EP2009/062824, dated May 19, 2011, 6 pgs.
McShane, Michael J. et al., "Glucose Monitoring Using Implanted Flourescent Microspheres", *IEEE Engineering in Medicine and Biology* XP-000975447 Nov./Dec. 2000, 10 pgs.

* cited by examiner

IMPLANTATION DEVICE FOR METABOLITE SENSORS

BACKGROUND

The invention relates to an implantation device for implanting a sensor element for detecting at least one analyte. Such sensor elements are used, in particular, to determine at least one metabolite concentration in a bodily fluid and/or body tissue. Such metabolites can for example, but not exclusively, comprise blood glucose, lactate, cholesterol or other types of analytes and metabolites. However, alternatively, or additionally, the sensor element can in principle also be used in other fields of analysis, for example in analytic chemistry, particularly in in situ analysis, process monitoring or similar fields.

Many conventional systems for determining analyte and metabolite concentrations are often based on generating a bodily fluid sample, e.g. a drop of blood, and subsequently examining the latter with respect to their analyte contents by using a suitable measurement instrument. By way of example, optical and/or electrochemical measurement methods can be used in this case.

In order to reduce the discomforts of the patients connected to the frequent generation of blood samples, different non-invasive or minimally-invasive techniques for measuring analyte concentrations have been developed. In the following text, determining the blood glucose concentration is discussed without restricting the scope of protection of the invention; however, of course it is the case that other types of analytes and metabolites can, alternatively or additionally, also be detected.

The invasive techniques for determining the analyte concentration are usually based on sensors which can be implanted into body tissue and/or a bodily fluid and which can determine the analyte concentration by optical and/or electrochemical means. In general, optical systems use at least one sensor material which changes at least one property which can be measured optically if one or more specific analytes are present. This property, which can be measured optically can be formed in the most diverse ways, with many different methods, sensor materials and measurement devices being known from the prior art. In principle, all of these known sensor materials can also be used within the scope of the present invention. However, within the scope of the present invention, sensor elements based on electrochemical measurement methods can also be used with the implantation device.

By way of example, WO 01/13783 describes an ocular sensor for glucose, which is designed as an ophthalmic lens. The ocular sensor comprises a glucose receptor as a sensor material, which glucose receptor is marked with a first fluorescent label, and a glucose competitor which is marked with a second fluorescent label ("donor"). The two fluorescent labels are selected such that if the competitor is bound to the receptor, the fluorescence of the second fluorescent label is quenched due to a resonant fluorescence energy transfer (quenching). By monitoring the change in the fluorescence intensity at a wavelength about the fluorescence maximum of the quenchable fluorescent label, the proportion of the fluorescence-marked competitor displaced by the glucose can be measured. This affords the possibility of determining the glucose concentration in the ocular fluid. The measurement can in turn be used to deduce the blood glucose concentration therefrom. Other types of detection are also feasible and known to a person skilled in the art, e.g. a fluorescence detection of the first fluorescent label.

WO 02/087429 describes a fluorophotometer by means of which blood glucose concentrations can be determined by measuring the glucose concentrations from the ocular fluid. The illustrated device is able to measure simultaneously two fluorescence intensities at different wavelengths.

There are different concepts for coupling optical signals into or out of the sensor elements, depending on the tissue type of the tissue into which the sensor element is implanted. In the sensor elements described in WO 01/13783 and WO 02/087429, the tissue layers which cover the implanted sensor are generally transparent in the region of the eye and thus make coupling in and out of light signals possible.

For non-transparent tissue types, WO 2005/054831 A1, for example, describes a sensor element for determining a glucose concentration which uses an optical waveguide. A sensor element is applied to the distal end of the optical waveguide, which sensor element comprises a binding protein which can bind with at least one target analyte. The sensor element furthermore comprises at least one reporter group which is subject to a change in luminescence if the analyte concentrations change. The sensor element optionally comprises reference groups with luminescent properties which do not change significantly if the analyte concentrations change.

U.S. Pat. No. 7,226,414 B2 also describes a glucose sensor device to be implanted within the subcutaneous tissue of an animal body. A sensor material is arranged in a first chamber, with glucose being able to enter into the first chamber from the body tissue. The sensor element furthermore comprises a reference chamber with a reference solution. The use of optical waveguide fibres which connect a detection instrument to the chambers is once again proposed for coupling a read-out instrument thereto.

U.S. 2007/0122829 A1 proposes a system, a device and a method for measuring the concentration of an analyte in a liquid or a matrix. A thermodynamically stabilized, analyte-binding ligand is proposed. In this case, the use of a separate optical waveguide which is in the form of a fibre and coupled to a sensor element is also proposed in turn, which optical waveguide connects a detection instrument with an implanted sensor element.

In particular, a challenge in the case of implantable sensor elements is to uniformly, reproducibly but nevertheless as painlessly as possible implant the sensor elements in the body tissue. Particularly in the case of sensor elements with optical coupling which are wholly or partly covered by a skin section, but also in the case of e.g. electrochemical sensor elements, the implantation depth and the sensor position significantly affect the signal quality. Furthermore, an implantation technique which is as minimally invasive as possible is desirable to ensure an implantation which is as painless as possible, and, subsequently, a removal of the sensor elements which is as painless as possible.

SUMMARY

An embodiment of the present invention provides an implantation device for implanting a sensor element in body tissue, which overcomes the difficulties described above. In particular, the implantation device should make a reproducible implantation of sensor elements possible, and ensure an embedding of the sensor elements into the body tissue which is as painless as possible.

DETAILED DESCRIPTION

In principle, the implantation device according to one or more embodiments can be used for implanting into body tissue sensor elements for detecting at least one analyte in a bodily fluid and/or body tissue. In particular, the sensor elements can comprise one or more of the sensor elements described above. The sensor elements can be used in particular to determine at least one metabolite concentration in a bodily fluid. Reference can be made to the above description in the background for possible examples of analytes. The term "detection" can in this case be understood as meaning a quantitative and/or qualitative determination of an analyte concentration, i.e. the amount and/or concentration of the analyte in the bodily fluid is determined and/or the question is answered as to whether the analyte is even contained in the bodily fluid.

In one embodiment, the implantation device comprises at least one cannula for piercing the skin surface of a patient. Within the scope of the present invention, a cannula is understood to be a substantially tube-like structure which can have a rigid or flexible design and which has an interior lumen. This interior lumen can have a constant or variable cross section. Instead of a single interior lumen, it is also possible for cannulae to be used which have a number of interior lumens and so afford the possibility of, for example, also producing and/or implanting multi-layered sensor elements. Thus, the cannula can, for example, comprise a number of lumens arranged around each other in an annular fashion in which, for example, different components of the sensor elements can be held. Neighbouring arrangements of a number of lumens are also feasible.

By way of example, it is possible for the skin surface to be cut in order to pierce the skin surface before using the implantation device. However, it is particularly preferred if the cannula itself has an element for piercing the skin surface, for example a cannula tip and/or an element with a sharp edge which is designed to perforate the skin surface.

The cannula can have at least one holding area for holding the sensor element. By way of example, this holding area can comprise a region between a cannula tip, which is inserted into the skin surface first, and a constriction within the cannula, e.g. a constriction within the interior lumen of the cannula. However, embodiments in which the holding area does not differ from the remainder of the interior lumen of the cannula are also feasible. In particular, the holding area can have a circular cylindrical design to hold circular cylindrical sensor elements, that is to say sensor elements with a circular cross section and an elongate form. By way of example, the holding area can have a diameter of between 100 µm and 1 mm, with particularly preferred diameters being in the range of between 200 and 500 µm. By way of example, lengths of between 1 mm and 8 mm, preferably of between 2 mm and 5 mm, lend themselves to the length of the holding area and hence to the length of the sensor elements.

Furthermore, in one or more embodiments, the implantation device has at least one hydraulic container, connected to the cannula, for holding a hydraulic fluid. The connection between the hydraulic container and the cannula can, for example, be effected rigidly and so the hydraulic container and the cannula together form an implantation unit. In particular, the cannula can be connected directly to the hydraulic container; however, alternatively, connections via intermediate elements, e.g. one or more tubes, are also possible.

In particular embodiments, the hydraulic container should, to a certain extent, have a pressure-resistant design. In principle, gasses and/or liquids lend themselves to being a hydraulic fluid, with liquids being preferred. The hydraulic fluid should preferably be designed to be biocompatible. Therefore, it is particularly preferred to use a saline, in particular a physiological saline, as a hydraulic fluid. However, it is also possible for different types of fluids to be used, as well as mixtures and combinations of different fluids.

The implantation device furthermore has at least one pressure generation device according to one or more embodiments. This pressure generation device should be designed to apply pressure, i.e. positive pressure and/or negative pressure, to the hydraulic fluid. In this way, by applying positive pressure to the hydraulic fluid in the hydraulic container and hence in the cannula, the sensor element can be transferred from the cannula into the body tissue by means of this pressurized hydraulic fluid, e.g. it can hydraulically be pushed into the body tissue.

The pressure generation device for generating the positive or negative pressure in the hydraulic container can, in particular, comprise at least one pressure piston which is hydraulically connected to the hydraulic container. By way of example, the pressure piston can be wholly or partly held within the hydraulic container. However, alternatively, or additionally, the pressure piston can also be held in a different element of the implantation device, e.g. in a separate pressure generator which is hydraulically connected to the hydraulic container, for example by means of a tube or pipe connection. However, in principle other types of pressure generators are also feasible, for example pressure generators with a separate pressure source, e.g. a pump, an external pressure source or the like.

It is particularly preferred if the implantation unit, comprising the cannula and the hydraulic container, can be moved as a whole relative to the pressure piston. By way of example, the implantation unit can be moved axially, that is to say along an axis of the implantation device, relative to the pressure piston. Here, it is particularly preferred if the pressure piston can be fixed in its position, e.g. its position relative to the skin surface of the patient, and so only the implantation unit is moved relative to the pressure piston and hence relative to the skin surface as well. To this end, the pressure piston can for example be connected to at least one resting surface for resting on the skin surface, for example via a piston rod. This resting surface can have components which are wholly or partly identical to those of a device which is also connected for setting and/or restricting the implantation depth.

Such a device for setting and/or restricting the implantation depth, which can also be provided independently of the design of the pressure generator and pressure piston, can significantly improve the reproducibility of implanting the sensor element. However, as illustrated above, this reproducibility is of decisive importance for the signal quality, particularly in the case of optical sensor elements. Therefore, for this reason it is proposed that the implantation device is provided with such a device.

In particular, such a device for setting and/or restricting the implantation depth can comprise a depth stop, for example a stopper, which restricts motion of the implantation device relative to the skin surface and hence restricts a penetration depth of the cannula into the skin surface. Hence, the device can for example comprise a resting surface for resting on the skin surface, which resting surface can therefore provide a fixed position relative to the skin surface. In particular, this resting surface can be a large-area resting surface, that is to say a resting surface with a size of a few ten square millimeters up to a few square centimeters. The resting surface can for example partly surround the cannula, or the cannula tip, annularly (e.g. in a circular annular fashion). As described above, the resting surface can in particular be connected to the pressure piston, for example via a piston rod.

If such a device for setting and/or restricting the implantation depth is provided, it is particularly preferred if the implantation unit, comprising the hydraulic container and the cannula, is connected to this device via at least one spring element. This spring element, which can for example be designed as a coil spring element or a leaf spring element but which can however alternatively, or additionally, comprise other types of elastic elements as well, can serve as a return spring and can promote pulling out the cannula from the body tissue once the implantation has been effected. In particular, the spring element can in turn be connected to the resting surface and can apply a pretension on this implantation unit relative to this resting surface or push the implantation unit away from this resting surface.

In a further preferred embodiment, the hydraulic container of the implantation device is connected to a hydraulic reservoir for holding and providing the hydraulic fluid via at least one connection. By way of example, this hydraulic reservoir can comprise a reservoir tank. The connection can for example comprise one or more tube connections which tolerate movement of the implantation unit relative to the hydraulic reservoir. However, alternatively, the hydraulic reservoir can also wholly or partly be fixedly connected to the implantation unit, for example to the hydraulic reservoir.

Furthermore, the connection can comprise at least one valve. It is particularly preferred if this valve comprises a check valve. Thus, by way of example, the valve can be designed to open in the case of negative pressure in the hydraulic container and permit subsequent flow of hydraulic fluid into the hydraulic container.

Particularly the last refinement of the implantation device makes particularly simple and reproducible implanting of the sensor elements possible. Thus, by way of example, the implantation unit with the hydraulic container and the cannula can be lowered with respect to the skin surface such that the cannula tip with the holding area penetrates the skin surface. The pressure generation device can be designed such that negative pressure is generated in the hydraulic container during this lowering. This can, for example, be effected, as described above, by using a fixed pressure piston. If the implantation device is lowered relative to this pressure piston, negative pressure is generated in the hydraulic container. Hydraulic fluid can then subsequently flow into the hydraulic container via the valve, in particular the check valve. If the implantation device is subsequently lifted again, driven, for example, by the return spring or the spring element, and the cannula is pulled out of the skin surface, the pressure increases again in the hydraulic container as a result of the fixed position of the pressure piston. Due to this pressure increase as a result of pulling the cannula out of the tissue, the sensor element is pushed out of the holding area of the cannula and into the tissue.

The advantage of this implantation design is that the implantation can be limited to handling the implantation unit and controlling the position of said implantation unit. A separate control for pushing out the sensor element out of the holding area of the cannula into the tissue is not necessary since this pushing out, or transferring, into the body tissue is effected automatically by means of the hydraulic fluid. Hence, the implantation movement is in general preferably coupled to the pressure generator such that an implantation movement automatically effects the transfer of the sensor element from the cannula into the body tissue.

Analogously, the implantation device can also be designed to remove the sensor element from the body tissue. Thus, for example, in order to remove the sensor element, a cannula corresponding to the sensor element can be inserted into the body tissue through the skin surface such that the sensor element is wholly or partly pushed into the opening of the cannula. The pressure generation apparatus can be correspondingly designed to generate negative pressure in the hydraulic fluid, as a result of which the sensor element can be sucked into the cannula. By way of example, the valve which connects the hydraulic reservoir and the hydraulic container can be closed for this purpose or a check valve acting in the opposite direction can be used. This affords the possibility of generating negative pressure in the hydraulic fluid when the implantation device is lowered, in which case the sensor element is wholly or partly inserted into the cannula or the holding area of the cannula, by means of which negative pressure the sensor element is completely sucked into the cannula. A different design of the pressure control is also possible, for example a pressure control in which the negative pressure is only effected during the subsequent renewed lifting, and hence removing, of the cannula out of the body tissue. Different refinements are feasible.

In order to prevent the sensor element to be removed from penetrating the cannula too deeply, in particular from penetrating beyond the holding area of the cannula, in particular when the sensor element is removed from the body tissue, the cannula can have at least one constriction, as described above. This constriction, which can for example be designed in the form of a neck of the interior lumen of the cannula and/or in the form of a conical constriction of the interior lumen of the cannula, prevents further penetration of the sensor element in the direction of the hydraulic container.

In a particularly preferred embodiment of the invention, the implantation device is designed such that the sensor element can wholly or partly be produced directly in the implantation device. Thus, for example, sensor elements can comprise crosslinkable materials which can be crosslinked directly in the cannula. By way of example, crosslinkable plastics can be used for this purpose, in particular crosslinkable hydrogels which can for example be crosslinked by a photochemical excitation. For this purpose it is particularly preferred if the cannula is at least partly transparent to electromagnetic radiation, in particular to light. In particular, transparency to light in the ultraviolet spectral range should be present. Accordingly, the implantation device can comprise at least one light source for crosslinking the at least one crosslinkable material of the sensor element in the cannula, for example a light source for generating ultraviolet radiation.

Hence, the proposed implantation device in one or more of the above-described embodiments permits reliable and very reproducible implanting of sensor elements with very different designs. The implantation can be effected painlessly and with a precisely prescribable implantation depth in different types of body tissue, with it for example being possible to implement the implantation depth by changing a setting (e.g. by using a set screw and/or an electromechanical device) of the implantation device. The implantation device or the implantation unit can be moved manually. However, alternatively, or additionally, automatic positioning or an automatic drive of the implantation unit can also be provided, for example a drive by means of one or more actuators which effect an advance and/or a retraction of the implantation unit, in particular the cannula, into and out of the body tissue respectively. On the one hand, the implantation can be effected in opaque body tissue, for example skin sections, or else in transparent tissue regions, such as a tissue region on the eye. Particularly the provision of a corresponding resting surface, which can be optimally matched to the bodily conditions in the region of the implantation site, can ensure a high reproducibility in this case.

Further details and features of the invention emerge from the following description of preferred exemplary embodiments in combination with the dependent claims. Here, the respective features can be realized independently or a number of them can be realized in combination with one another. The invention is not restricted to the exemplary embodiments. The exemplary embodiments are illustrated schematically in the figures. Identical reference symbols in the individual figures in this case refer to identical or functionally identical elements, or elements which correspond to one another with respect to their functions.

DETAILED DESCRIPTION

Figure 1:
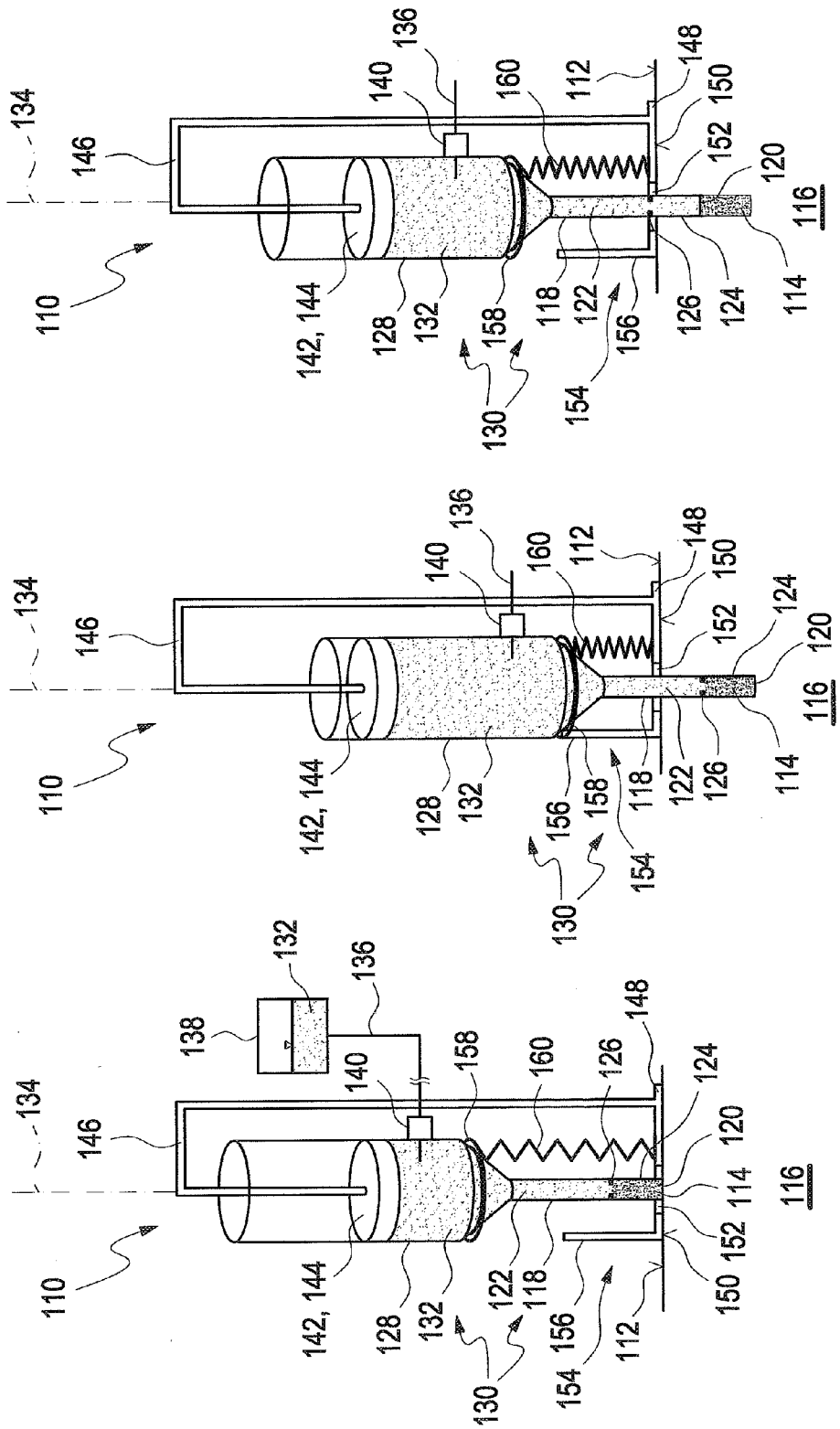
FIGS. 1A to 1C show an implantation device according to the invention in different stages of an implantation procedure.

FIGS. 1A to 1C show, from the side, a schematic illustration of an implantation device 110 according to the invention. At the same time, FIGS. 1A to 1C, which show different stages of an implantation procedure of a sensor element 114 through a skin surface 112 into a tissue 116, are used to explain a possible exemplary embodiment of an implantation procedure using the implantation device 110.

The implantation device 110 comprises a cannula 118 with an implantation tip 120 at the end thereof which faces the tissue 116. In the figures, this implantation tip 120 is designed as a blunt implantation tip 120. However, alternatively this implantation tip 120 can also be designed with a sharp-edged or pointed element, for example by, as is usual in many cannulae, bevelling the implantation tip 120 and hence designing the latter with a sharp edge. In this fashion, no separate instrument for generating an opening in the skin surface 112 is necessary; rather, the implantation tip 120 itself can create the opening in the skin surface 112 required for penetrating the tissue 116.

In the simple exemplary embodiment illustrated in the figures, the cannula 118 is illustrated as a cylindrical cannula 118 with a cylindrical interior lumen 122. However, other refinements are also possible.

A holding area 124 is provided on the end of the interior lumen 122 facing the implantation tip 120. This holding area 124 is used to hold the sensor element 114 and is restricted at its upper end facing away from the implantation tip 120 by a constriction 126 in the cannula 118. In the illustrated exemplary embodiment, the constriction 126 is designed as a bead on the interior wall, that is to say as an inwardly projecting thickening of the wall of the cannula 118. However, in principle, other refinements are also possible.

At its upper end facing away from the implantation tip 120, the cannula 118 is connected to a hydraulic container 128. Here, a fixed connection between cannula 118 and hydraulic container 128 is provided in FIGS. 1A to 1C and so the hydraulic container 128 and the cannula 118 together form an implantation unit 130 which, in the illustrated exemplary embodiment, is designed as a rigid implantation unit. Here, in the illustrated exemplary embodiment, the connection between the hydraulic container 128 and the cannula 118 is designed in the shape of a funnel and so hydraulic liquid 132, e.g. physiological saline, held in the hydraulic container 128 can easily flow from the hydraulic container 128 into the cannula 118. However, in principle, other refinements are also possible, e.g. a tube connection and/or a pipe connection between the hydraulic container 128 and the cannula 118. Here, in the illustrated exemplary embodiment, the cannula 118 and the hydraulic container 128 are aligned concentrically with respect to an axis 134. Naturally, different embodiments are also possible in this respect.

A connection 136 connects the hydraulic container 128 to a hydraulic reservoir 138, the latter only being illustrated in FIG. 1A and only being illustrated schematically. Here, in the illustrated exemplary embodiment, the connection 136 comprises a valve 140, for example a valve such as a check valve which opens inwardly into the interior of the hydraulic container 128. Thus, if there is negative pressure in the interior of the hydraulic container 128, this valve 140 opens and hydraulic liquid 132 from the hydraulic reservoir 138 can subsequently flow into the hydraulic container 128.

In the illustrated exemplary embodiment, the implantation device 110 furthermore comprises a pressure generation device 142 for generating positive and/or negative pressure within the hydraulic container 128. In the illustrated exemplary embodiment, this pressure generation device 142 comprises a pressure piston 144 which is connected to a piston rod 146. This piston rod 146 in turn is connected to a rest 148 with a resting surface 150 for resting on the skin surface 112. This rest 148 has an opening 152 which surrounds the cannula 118 annularly and through which the cannula 118 can be lowered into the tissue 116. Thus, the implantation unit 130 as a whole can be moved axially, i.e. along the axis 134, relative to the pressure piston, the piston rod 146 and the rest 148.

In the exemplary embodiment illustrated in the figures, the implantation device 110 furthermore has a device 154 for restricting and/or setting the implantation depth. The device 154 comprises the rest 148 with the resting surface 150 and the opening 152. Furthermore, the device 154 comprises a depth stop 156, which for example protrudes perpendicularly from the rest 148 and acts as a stopper. As can be seen, for example, in FIG. 1B, the depth stop 156 is designed to impact on a ring element 158 holding the hydraulic container 128 in the funnel-shaped transition region to the cannula 118 and in this fashion limit the penetration depth of the cannula 118 into the tissue 116.

The device 154 or the implantation device 110 furthermore comprises a spring element 160. This spring element 160, which for example can be designed as a coil spring, simultaneously serves as a return spring and is supported at one end on the rest 148 and on the hydraulic container 128 or the ring element 158 at the other end. This compresses the spring element 160 when the cannula 118 penetrates the tissue 116 such that the penetration of the cannula 118 must be effected against the elasticity of said spring element 160. By contrast, the upward motion, as a result of which the cannula 118 is again pulled out of the tissue 116, is preferably effected with the support of the elasticity of the spring element 160.

Using the sequence of figures in FIGS. 1A to 1C, a typical implantation procedure is intended to be explained. However, in principle, other refinements of the implantation procedure or the implantation device 110 are also possible.

In the initial state, illustrated in FIG. 1A, the implantation unit 130 is above the skin surface 112. The sensor element 114 is held in the holding area 124. With respect to this, reference is made to the fact that the sensor element 114 can also wholly or partly be produced in this state. To this end, the cannula 118 can, for example, be designed as a transparent cannula, at least in the region of the holding area 124. In this case, transparent plastics, transparent ceramics or glass, for example, can be used as cannula material instead of steel or other metallic materials. Composite materials are also possible. By way of example, the implantation device 110 can comprise a light source (not illustrated in the figures) which illuminates the holding area 124 from the outside such that polymerization of the sensor element 114 can occur in the holding area 124. However, alternatively, an already finished sensor element 114 can also be loaded into the holding area 124 so as to then bring the implantation device 110 into the initial state illustrated in FIG. 1A in which the rest 148 rests on the skin surface 112.

Subsequently, the implantation unit 130 is lowered relative to the rest 148, as illustrated in FIG. 1B. By way of example, this lowering can be effected manually or driven by one or more actuators. The actuator is not illustrated in the figures and can, for example, be connected between the rest 148 and the implantation unit 130 in order to drive a relative motion of these elements 130, 148. This refinement using at least one actuator offers the advantage of the speed of the penetration into the tissue 116 being able to be developed particularly evenly, which can ensure an evenness of the implantation and an implantation which is as painless as possible. For the purpose of the cannula 118 penetrating the tissue 116, an opening in the skin surface 112 can be generated separately, or the cannula 118 itself can be designed with a sharp end, as described above.

In accordance with FIG. 1B, the implantation unit 130 is lowered until the ring element 158 impacts against the depth stop 156. By way of example, the depth stop 156 can also be designed as an adjustable depth stop such that the penetration depth and hence the implantation depth can be influenced in a targeted manner. Alternatively, or additionally, it is also possible for e.g. the position of the ring element 158 to be changed in order to set the implantation depth. Other possibilities are also feasible. During the lowering, the pressure piston 144, by using the piston rod 146, preferably remains in a fixed position with respect to the skin surface 112 such that this pressure piston 144 de facto lifts within the hydraulic container 128 and that the volume within the hydraulic container 128 available to the hydraulic liquid 132 increases. This briefly generates negative pressure within the hydraulic container 128. As a result of this negative pressure, the check valve 140 opens and hydraulic liquid 132 can subsequently flow from the hydraulic reservoir 138 into the interior of the hydraulic container 128.

After the downward motion along the axis 134 illustrated in FIG. 1B, during which the cannula 118 penetrates the tissue 116, there is, in accordance with FIG. 1C, a subsequent upward motion of the implantation unit 130, likewise in the direction of the axis 134. In the process, the cannula 118 is pulled out of the tissue 116. Again, the pressure piston 144 remains in a fixed position relative to the skin surface 112 and so the implantation unit 130 in turn moves upward relative to this pressure piston 144. This increases the pressure of the hydraulic liquid 132 in the interior of the hydraulic container 128 since the valve 140 now closes. As a result of this hydraulic pressure, the sensor element 114 is pushed out of the holding area 124 of the cannula 118 into the tissue 116 and separated from the cannula 118. The implantation procedure has thus been completed.

Figure 2:
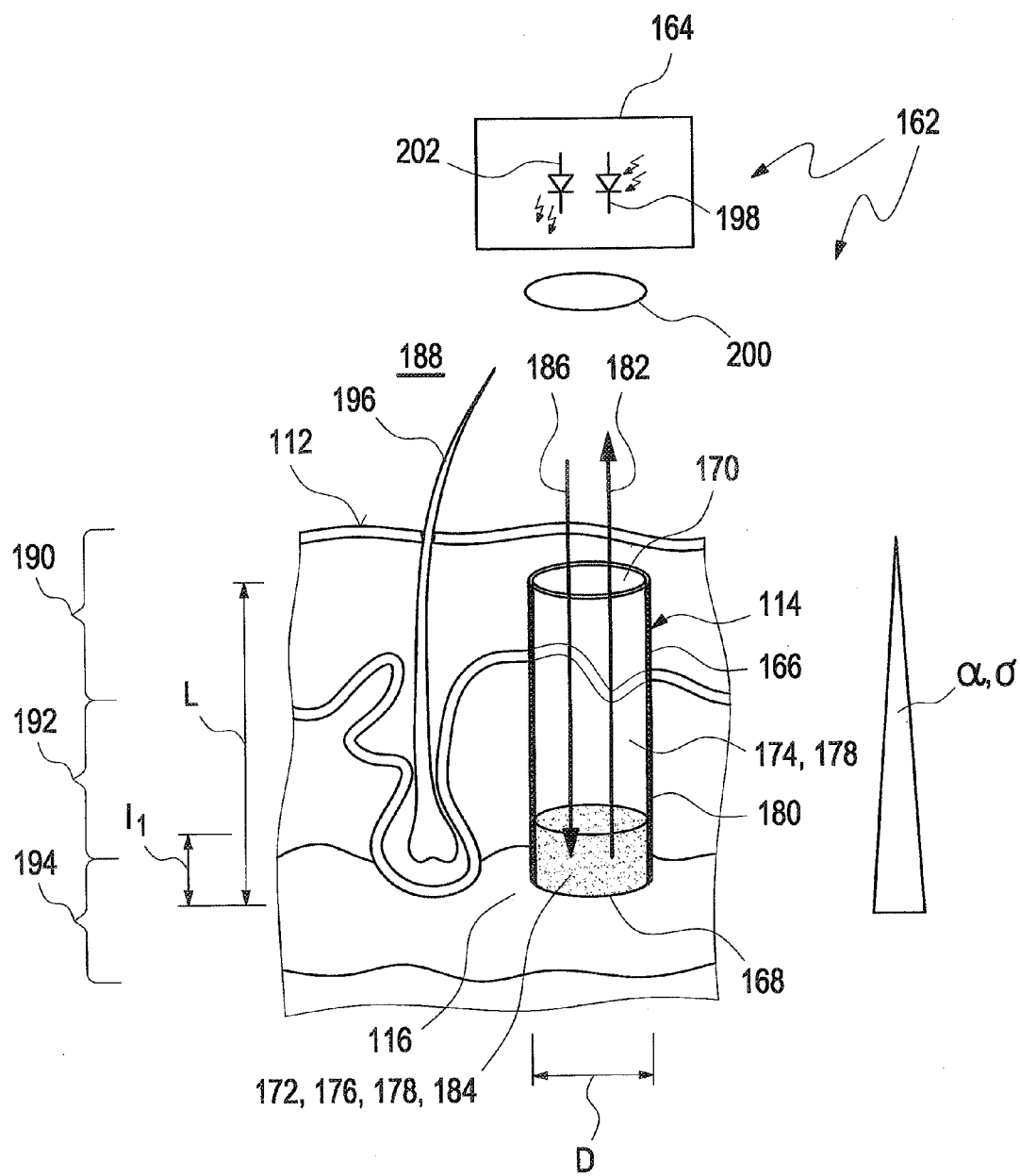
FIG. 2 shows a sensor element implanted into body tissue.

FIG. 2 illustrates an exemplary embodiment of a sensor arrangement 162 which comprises a detection device 164 and a sensor element 114 implanted by means of the implantation device 110, e.g. in accordance with the exemplary embodiment of FIGS. 1A to 1C. In principle, the implantation device 110 can be used to implant a multiplicity of sensor elements 114, with FIG. 2 only illustrating a specific exemplary embodiment in an implanted state. The sensor element 114 has an integral mould 166 with a sensor end 168 and a coupling end 170. In this exemplary embodiment, the mould 166 is for example designed as a continuous hydrogel mould. The mould 166 has a substantially cylindrical form, with a diameter D of approximately 200 to 500 μm and an overall length L of approximately 2 to 5 mm. Here, the sensor element 114 is subdivided into a sensor region 172, which in the implanted state points toward the interior of the tissue 116, and a transparent coupling part 174. The sensor region 172 has a length $l_1$ of approximately 200 to 500 μm. In the sensor region 172, a sensor material 176 is embedded in a matrix material 178, the matrix material 178 for example also possibly being present in the region of the coupling part 170. By way of example, the matrix material 178 can comprise a transparent hydrogel.

Furthermore, FIG. 2 also illustrates that the sensor element 114 can optionally be surrounded by a coating 180, e.g. a biocompatible coating and/or a coating with a curative active ingredient. The coating 180 can, for example, be applied to the mould 166 using a layer-by-layer method and/or a plasma coating method.

Furthermore, FIG. 2 illustrates that the transparent coupling part 174 serves as a "window" for coupling out an optical signal 182. This optical signal 182 can, for example, comprise light emitted and/or reflected by the sensor material 176, with emitted light being able to be emitted for example in the form of fluorescent light and/or luminescent light. This optical signal 182 of the sensor material 176 is preferably sensitive to the presence of an analyte in the body tissue 116 surrounding the sensor end 168. Furthermore, in addition to the sensor material 176, the sensor region 172 can also comprise a reference material 184 which can likewise contribute to the optical signal 182 and can reflect or emit a reference component of this optical signal 182. Furthermore, FIG. 2 illustrates an optional excitation beam 186 by means of which for example the sensor material 176 and/or the reference material 184 can specifically be excited. Whether it is necessary to use such an excitation beam 186 depends on the type of sensor material 176 and/or reference material 184 and/or the optical detection mechanism used to detect the at least one analyte in the body tissue 116 and/or in a bodily fluid which surrounds the sensor region 172. The coupling part 174 can serve as an optical waveguide, but can also be designed as a simple, homogeneous and transparent window without optical waveguide properties. In this case the coupling part 174 only acts as window for observing the sensor region 172 from the external region 188 outside of the skin surface 112.

Here, it can be seen in the exemplary embodiment in accordance with FIG. 2 that the sensor element 114 is preferably implanted into the body tissue 116 such that the coupling end 170 of said sensor element is still arranged below the skin surface 112. The skin surface 112 above the coupling end 170 is preferably already healed again during measurement operation.

As an example of body tissue 116, the exemplary embodiment illustrated in FIG. 2 shows a skin section with an epidermis 190, a dermis 192 and a hypodermis 194, with a hair 196 being illustrated as a size comparison example. Furthermore, FIG. 2 symbolically plots the absorption α and the scattering σ. Here, it can be seen that in the region of the skin surface 112, the scattering σ and the absorption α are low and increase with increasing depth in the interior of the body tissue 116. Reference is made to the fact that the illustrated skin section should only be understood as an example for a location of the implantation and therefore implantation can also occur in different types of body tissue 116, such as a tissue within an eye or in other types of body tissue as well.

In the exemplary embodiment in accordance with FIG. 2, the sensor arrangement 162 comprises the detection device 164 in addition to the sensor element 114. Provided that optical detection methods and optical sensor elements 114 are used, the detection device 164 for example has at least one optical detector 198. If different types of sensor elements 114 are used, different types of detection devices can correspondingly be provided, e.g. electrical detection devices, for example, for detecting a charge, a voltage or a current.

The optical detector 198 is only illustrated symbolically in FIG. 2 and is in this case symbolized as a photodiode. However, it is possible for provision to be made of a multiplicity of optical detectors and/or additional devices, e.g. devices for spectral separation of the optical signal 182, in order to detect the optical signal 182 from the sensor material 176 and/or the reference material 184 in an optimal fashion and possibly in a spectrally resolved fashion in particular. Here, the detection device 164 in FIG. 2 is designed such that it can be coupled to the coupling end 170 of the sensor element 114, with it preferably being possible for the coupling to be effected through the uppermost layers of the body tissue 116. By way of example, the detection device 164 can be placed onto the skin surface 112 for this purpose. In FIG. 2, the detection device 164 is optionally provided with additional optical devices 200 which are likewise only illustrated symbolically and which can for example comprise corresponding optics such as lenses, objectives, diaphragms or the like.

Furthermore, in the exemplary embodiment illustrated in FIG. 2, the detection device 164 optionally comprises at least one radiation source 202 for generating the optional excitation beam 186. The radiation source 202 is in turn illustrated symbolically as a light-emitting diode, but a multiplicity of different types of radiation sources can be comprised by this.

In addition to the optical device 200, the optical detector 198 and the radiation source 202, the detection device 164 can furthermore comprise additional components such as input and output means, energy supplies, data processing devices or the like. This optionally makes it possible for the signal generated by the implanted sensor 114 to be processed and, for example, be converted into an analyte concentration. By way of example, direct display of this analyte concentration to a user can, optionally, also be possible.

The invention claimed is:

1. An implantation device for implanting a sensor element for detecting at least one analyte in a bodily fluid or body tissue, comprising at least one cannula for piercing a skin surface of a patient, wherein the cannula has at least one holding area for holding the sensor element, wherein the implantation device has at least one hydraulic container, connected to the cannula, for holding a hydraulic fluid, wherein the implantation device has at least one pressure generation device, wherein the pressure generation device is designed to apply pressure to the hydraulic fluid, wherein the sensor element can be transferred from the cannula into the body tissue by a hydraulic pressure exerted by the hydraulic fluid, wherein the hydraulic fluid is supplied by a hydraulic reservoir into the hydraulic container via at least one connection and, wherein the connection comprises at least one valve, wherein the valve is designed to open in the case of negative pressure in the hydraulic container and permit subsequent flow of hydraulic fluid into the hydraulic container.

2. The implantation device according to claim 1, further comprising at least one device for setting and/or restricting the implantation depth, and wherein said at least one valve comprises a check valve.

3. The implantation device according to claim 2, wherein the device for setting and/or restricting the implantation depth comprises a resting surface for resting on the skin surface, wherein the resting surface at least partly annularly surrounds the cannula.

4. The implantation device according to claim 2, wherein the cannula and the hydraulic container form an implantation unit, with the device for setting and/or restricting the implantation depth being connected to the implantation unit via at least one spring element.

5. The implantation device according to claim 1, wherein the pressure generation device comprises at least one pressure piston held in the hydraulic container.

6. The implantation device according to claim 5, wherein the cannula and the hydraulic container form an implantation unit, with the implantation unit being movable axially along an axis of the implantation device, relative to the pressure piston.

7. The implantation device according to claim 5, wherein a position of the pressure piston can be fixed relative the skin surface, wherein the pressure piston is connected to at least one resting surface.

8. The implantation device according to claim 1, wherein the hydraulic fluid comprises a saline.

9. The implantation device according to claim 1, wherein the cannula is at least partly transparent to light in the ultraviolet spectral range.

10. The implantation device according to claim 9, further comprising at least one light source for crosslinking, and in the cannula, at least one material of the sensor element which can be crosslinked.

11. The implantation device according to claim 1, wherein the cannula has at least one constriction for limiting the holding area.

12. The implantation device according to claim 1, wherein the implantation device is designed to remove a sensor element implanted in the body tissue, wherein the pressure generation device is designed to generate negative pressure in the hydraulic fluid to allow the sensor element to be sucked into the cannula.

13. The implantation device according to claim 1, further comprising at least one sensor element for detecting at least one analyte in a bodily fluid or body tissue.

14. The implantation device according to claim 1, further comprising at least one device for setting and/or restricting the implantation depth, wherein the device for setting and/or restricting the implantation depth comprises a resting surface for resting on the skin surface, wherein the resting surface at least partly annularly surrounds the cannula, and wherein the cannula and the hydraulic container form an implantation unit, with the device for setting and/or restricting the implantation depth being connected to the implantation unit via at least one spring element.

15. The implantation device according to claim 14, wherein the valve is designed to open in the case of negative pressure in the hydraulic container and permit subsequent flow of hydraulic fluid into the hydraulic container.

16. The implantation device according to claim 15, wherein the cannula and the hydraulic container form an implantation unit, with the implantation unit being movable axially along an axis of the implantation device, relative to the pressure piston.

17. The implantation device according to claim 16, wherein a position of the pressure piston can be fixed relative the skin surface, wherein the pressure piston is connected to at least one resting surface.

18. The implantation device according to claim 17, wherein the cannula is at least partly transparent to light in the ultraviolet spectral range and further comprising at least one light source for crosslinking, and in the cannula, at least one material of the sensor element which can be crosslinked.

19. The implantation device according to claim 18, wherein the cannula has at least one constriction for limiting the holding area and further comprising at least one sensor element for detecting at least one analyte in a bodily fluid or body tissue.

20. The implantation device according to claim 2, wherein the at least one device for setting and/or restricting the implantation depth is a depth stop.

21. The implantation device according to claim 7, wherein the at least one resting surface is the resting surface of the device for setting and/or restricting the implantation depth.

22. The implantation device according to claim 8, wherein the saline is a physiological saline.

23. The implantation device according to claim 14, wherein the at least one device for setting and/or restricting the implantation depth is a depth stop.

24. The implantation device according to claim 17, wherein the at least one resting surface is the resting surface of the device for setting and/or restricting the implantation depth.

25. An implantation device for implanting a sensor element for detecting at least one analyte in a bodily fluid or body tissue, comprising at least one cannula for piercing a skin surface of a patient, wherein the cannula has at least one holding area for holding the sensor element, wherein the implantation device has at least one hydraulic container, connected to the cannula, for holding a hydraulic fluid, wherein the implantation device has at least one pressure generation device, wherein the pressure generation device is designed to apply pressure to the hydraulic fluid, wherein the sensor element can be transferred from the cannula into the body tissue by a hydraulic pressure exerted by the hydraulic fluid, wherein the hydraulic fluid is supplied by a hydraulic reservoir into the hydraulic container via at least one connection and, wherein the connection comprises at least one valve, wherein the pressure generation device comprises at least one pressure piston held in the hydraulic container, wherein a position of the pressure piston can be fixed relative the skin surface, wherein the pressure piston is connected to at least one resting surface, the connection being effected by means of a piston rod.

26. An implantation device for implanting a sensor element for detecting at least one analyte in a bodily fluid or body tissue, comprising at least one cannula for piercing a skin surface of a patient, wherein the cannula has at least one holding area for holding the sensor element, wherein the implantation device has at least one hydraulic container, connected to the cannula, for holding a hydraulic fluid, wherein the implantation device has at least one pressure generation device, wherein the pressure generation device is designed to apply pressure to the hydraulic fluid, wherein the sensor element can be transferred from the cannula into the body tissue by a hydraulic pressure exerted by the hydraulic fluid, wherein the hydraulic fluid is supplied by a hydraulic reservoir into the hydraulic container via at least one connection and, wherein the connection comprises at least one valve, wherein the cannula is at least partly transparent to light in the ultraviolet spectral range.

27. An implantation device for implanting a sensor element for detecting at least one analyte in a bodily fluid or body tissue, comprising at least one cannula for piercing a skin surface of a patient, wherein the cannula has at least one holding area for holding the sensor element, wherein the implantation device has at least one hydraulic container, connected to the cannula, for holding a hydraulic fluid, wherein the implantation device has at least one pressure generation device, wherein the pressure generation device is designed to apply pressure to the hydraulic fluid, wherein the sensor element can be transferred from the cannula into the body tissue by a hydraulic pressure exerted by the hydraulic fluid, wherein the hydraulic fluid is supplied by a hydraulic reservoir into the hydraulic container via at least one connection and, wherein the connection comprises at least one valve, wherein the implantation device is designed to remove a sensor element implanted in the body tissue, wherein the pressure generation device is designed to generate negative pressure in the hydraulic fluid to allow the sensor element to be sucked into the cannula.

28. An implantation device for implanting a sensor element for detecting at least one analyte in a bodily fluid or body tissue, comprising at least one cannula for piercing a skin surface of a patient, wherein the cannula has at least one holding area for holding the sensor element, wherein the implantation device has at least one hydraulic container, connected to the cannula, for holding a hydraulic fluid, wherein the implantation device has at least one pressure generation device, wherein the pressure generation device is designed to apply pressure to the hydraulic fluid, wherein the sensor element can be transferred from the cannula into the body tissue by a hydraulic pressure exerted by the hydraulic fluid, wherein the hydraulic fluid is supplied by a hydraulic reservoir into the hydraulic container via at least one connection and, wherein the connection comprises at least one valve; further comprising at least one device for setting and/or restricting the implantation depth, wherein the device for setting and/or restricting the implantation depth comprises a resting surface for resting on the skin surface, wherein the resting surface at least partly annularly surrounds the cannula, and wherein the cannula and the hydraulic container form an implantation unit, with the device for setting and/or restricting the implantation depth being connected to the implantation unit via at least one spring element; wherein the valve is designed to open in the case of negative pressure in the hydraulic container and permit subsequent flow of hydraulic fluid into the hydraulic container.

* * * * *